(12) United States Patent
Huang et al.

(10) Patent No.: US 8,192,382 B2
(45) Date of Patent: Jun. 5, 2012

(54) DEVICE TO TREAT AND/OR PREVENT SHOULDER SUBLUXATION

(76) Inventors: Ying Chi Huang, Flushing, NY (US); Manuj Agarwal, Fresh Meadows, NY (US)

( * ) Notice: Subject to any disclaimer, the term of this patent is extended or adjusted under 35 U.S.C. 154(b) by 436 days.

(21) Appl. No.: 12/287,513

(22) Filed: Oct. 10, 2008

(65) Prior Publication Data

US 2009/0149789 A1 Jun. 11, 2009

Related U.S. Application Data

(60) Provisional application No. 61/000,009, filed on Oct. 24, 2007.

(51) Int. Cl.
*A61F 5/00* (2006.01)
(52) U.S. Cl. ............................................. 602/13; 602/4
(58) Field of Classification Search ................... 602/4–5, 602/19, 20–22; 128/875, DIG. 19; 2/44, 2/45
See application file for complete search history.

(56) References Cited

U.S. PATENT DOCUMENTS

| 4,446,858 A | 5/1984 | Verter | |
|---|---|---|---|
| 5,020,515 A | 6/1991 | Mann et al. | |
| 5,188,587 A | 2/1993 | McGuire et al. | |
| 5,407,421 A | 4/1995 | Goldsmith | |
| 6,110,133 A * | 8/2000 | Ritts | 602/4 |
| 6,398,746 B2 * | 6/2002 | Bramlage et al. | 602/5 |
| 7,320,669 B2 * | 1/2008 | Campbell et al. | 602/4 |
| 2007/0118993 A1 * | 5/2007 | Bates | 5/655.3 |

* cited by examiner

*Primary Examiner* — Michael A. Brown

(57) ABSTRACT

A device intended to provide stabilization of a subluxed joint through a pneumatic air chamber combined with a plurality of straps designed to provide ease of use to the patient with a subluxed shoulder joint. This pneumatic sling will allow the user to operate this device with one upper extremity and improves independence to this population. The combination of the air chamber to the sling will provide added comfort by conforming to the discrepancies of an individual's body contours. The design of this invention with the manual pump and release valve will allow the ease of donning and doffing the device.

25 Claims, 9 Drawing Sheets

DEVICE TO TREAT AND/OR PREVENT SHOULDER SUBLUXATION

The present application claims the priority benefit of U.S. Provisional application Ser. No. 61/000,009, filed Oct. 24, 2007

BACKGROUND OF THE INVENTION

This invention relates a device for prevention and treatment of shoulder subluxation in patients with neurological dysfunction, such as stroke, or a number of other conditions that would impair the stability of the glenohumeral joint.

A stroke is an acute onset of neurological dysfunction caused by a malfunction in cerebral blood circulation which results in functional deficits congruent with the corresponding focal areas that are involved. A large variety of clinical manifestations may occur including varying levels of consciousness, sensory, motor, cognitive, perceptual, and language deficits. For the purpose of this background we will speak of the motor deficits involved that deem this device necessary.

In the initial stages of this disease process the patient will be flaccid: the patient has no voluntary control, muscles lack tone, and movement is not possible. During this flaccidity period of the cerebral vascular accident proprioceptive control may be shut off. This combined with the lack of tone and muscle paralysis decrease the support and normal seating of the rotator cuff muscles, especially the supraspinatus. The ligaments and capsule now becomes the shoulder's sole support. With the weight of the arm and gravity these structures may become stretched out and thus result in a shoulder subluxation. The gravitational forces and constant traction will result in persistent misalignment which will later cause pain.

Due to the fact that a stroke often impairs one side of the body many patients will find it hard to operate a traditional sling or as a matter of fact any arm sling. The dexterity of the effected side is compromised and the use of the one good arm is often insufficient to tighten the sling; the present invention is developed to accommodate this problem.

U.S. Pat. No. 5,188,587 of McGuire et al. discloses a shoulder brace comprising a shoulder sleeve and a plurality of straps. While the device serves a rehabilitative function for the shoulder joint, it does not conform to individual body contours and asymmetries. Furthermore, the McGuire et al. device does not adequately serve the function of treating shoulder subluxation for there is no mechanism of adequately lifting the humerus into the glenoid fossa. Rather, strap 206 is shown to depress the acromioclavicular joint which may cause further orthopedic problems.

U.S. Pat. No. 4,446,858 of Verter discloses a shoulder brace that serves to support the arm and shoulder in the event of lack of muscle tone and ligament integrity, as is the case in shoulder subluxation. While the device adequately serves this purpose, it does not allow the user ease of independent application without the help of another individual. Similar to McGuire, the device does not contour to different body shapes and asymmetries. This may result in areas of increased pressure which may cause pressure ulcers in patients with reduced tactile sensation. Indeed, pressure applied by the device is not uniform over the applied area.

It would be advantageous to the shoulder subluxation patient if the aforementioned deficiencies were addressed. It is the object of the invention to provide a shoulder brace that will maintain the integrity of the shoulder joint. It is a further object of the invention to provide a brace that will provide ease of independent use. It is a further object of the invention to provide a brace that will adjust to an individual's body counters and asymmetries to provide uniform support of the shoulder joints. It is a further object of the invention to provide a shoulder brace that will maintain the position of the humerus in the glenoid fossa and prevent shoulder subluxation.

SUMMARY OF THE INVENTION

The purpose of this invention is to aid in the reduction of a subluxation that one may have upon suffering a cerebral vascular accident also known as a stroke. Although slings for shoulder subluxation have already been developed, this invention differs from the prior art in many ways. The components in this device greatly add to the comfort of the wearer for it provides functional adaptations that improve the ease of independent use.

The component innovations in this device include one or more air chamber(s) that contours and conform to the shoulder region, strategically placed chest, shoulder and elbow straps that provide shoulder support that reduce subluxations at proper vectors. The chamber(s) possess a manual inflation mechanism and releasing mechanism existing on the external surface, as well as a cushioning medium that contacts the skin.

The component air chamber(s) contours at the shoulder region and is situated on the deltoids and the upper trapezius muscle. It is made of an airtight material and is specifically designed to allow proper gapping that would accommodate to the variances in body shape and sizes. As it is inflated the chamber would provide a snug fit that is unobtainable in the prior art. Previously invented shoulder slings make use of adjusting straps; instead of adjusting straps that go around the arm this device inflates to the proper fit thereby eliminating unnecessary clips and straps that would cause unwanted points of pressure.

In addition to providing a snug fit, this device upon inflation provides a uniform area of pressure around the shoulder joint thus reducing the risk of pressure ulcers. Moreover, an elbow support will provide lift via elbow straps of the humerus into the glenoid fossa thereby reducing the shoulder subluxation and providing increased stability. As the chamber is inflated the shoulder is further brought up into the glenoid fossa. The component straps strategically placed at the chest, shoulder and elbow region provide the correct vectors that produces lift in the correct angles in this device. They allow support in the correct direction to maintain stability while providing comfort to the wearer.

The component manual inflation mechanism existing on the external surface of the shoulder sleeve is specifically designed with the patient in mind. Upon having a cerebral vascular accident many patients find that they only have the use of one arm. With the development of this innovation the wearer can adjust the shoulder sling on a day to day basis independently. The wearer only needs to use one or two fingers to inflate the chamber to the desired fit at the shoulder. The wearer only needs to use one finger to release the air in the sling by pressing the release valve; this provides ease with removal.

The advent of this light-weight device will not only reduce shoulder subluxation and allow easier access, functional independence with regards to the donning and doffing of the shoulder sling, greater acceptance and regular use which will be followed with greater compliance.

PARTS LIST

Figure 1:
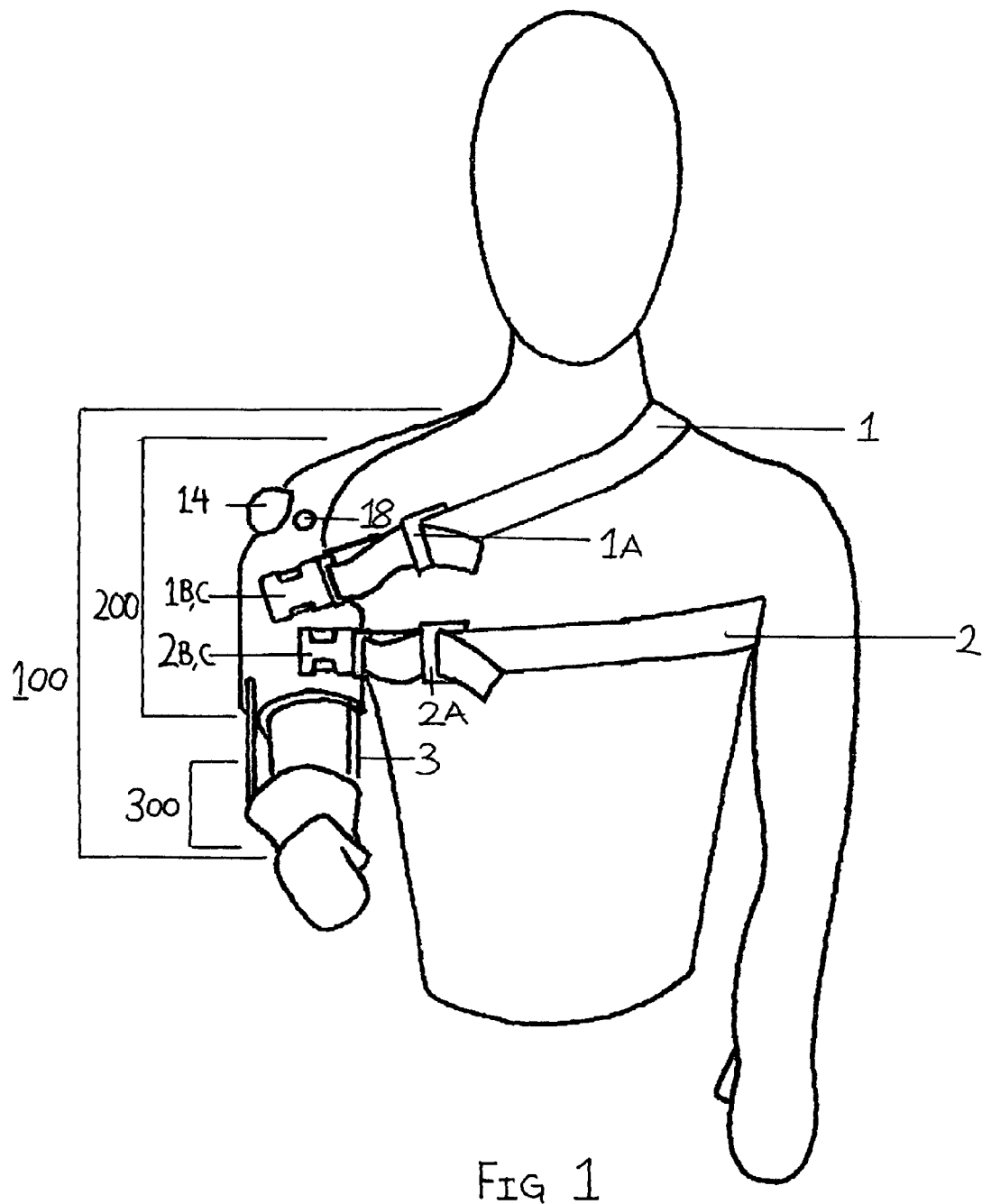
FIG. 1 is a view of the shoulder sling in accordance with the present invention as worn by a user

100: Shoulder sling device
200: shoulder sling portion
300: elbow elevating support
400: open region
1: strap 1
1A: length adjusting mechanism
1B: attachment element
1C: attachment retaining element
2: strap 2
2A: length adjusting mechanism
2B: attachment element
2C: attachment retaining element
3: Strap 3
3A: length adjusting mechanism
3B: elbow strap retaining mechanism
3C: strap looping element
4: cushioning element housing wall
4A: cushioning element
5: interior textile layer
6: exterior textile layer
7: exterior textile layer
8: air bladder
9: continuous air bladder space
10: air bubbles
10A: Air bubble inlet
11: ventilation holes
12: cushioning element housing wall
12A: cushioning element
13: interior textile layer
14: inflation mechanism
14A: collapsible inflation mechanism housing
15: inflation mechanism chamber area
15A: inflation mechanism retaining element
16: one way valve
17: one way valve
18: pressure releasing mechanism
19: pressure releasing mechanism housing
19A: pressure releasing mechanism retaining element
20: pressure releasing air outlets
21: pressure releasing valve
21A: air passage mechanism
21B: airtight lining element
22: buoyant pressure retaining mechanism

DETAILED DESCRIPTION OF THE PREFERRED EMBODIMENTS

Figure 2:
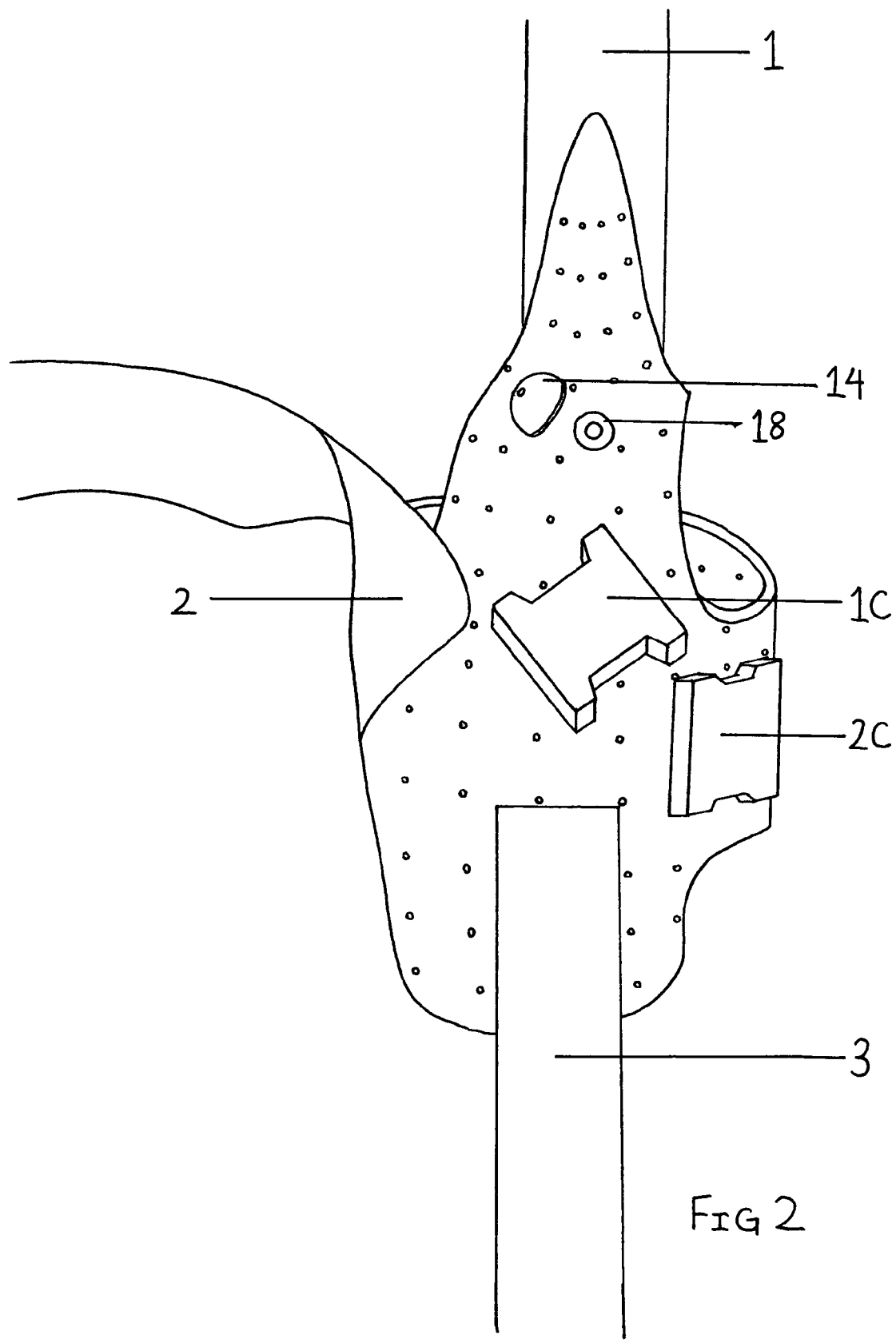
FIG. 2 is a perspective view of the anteriolateral portion of the shoulder sling.
Figure 3:
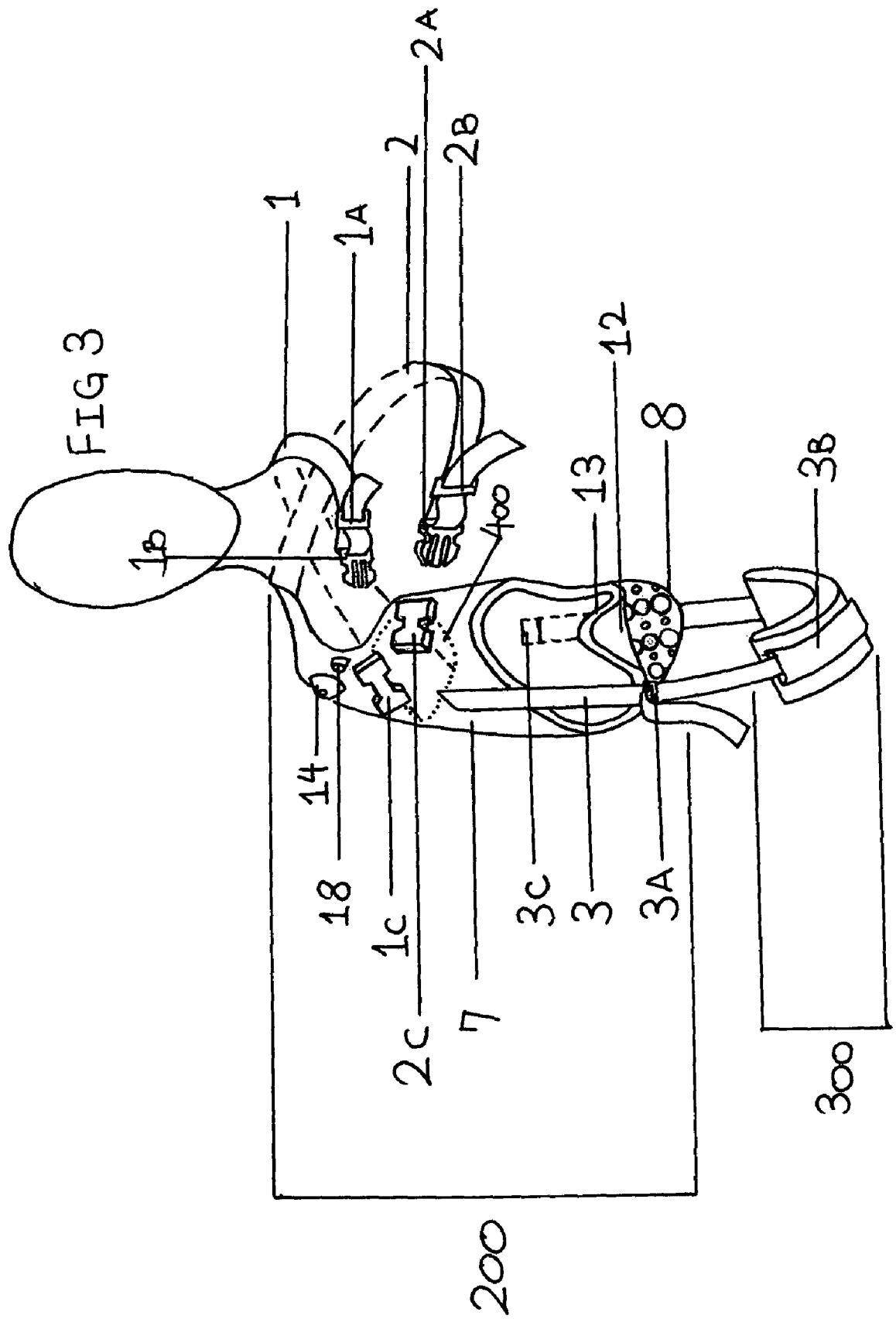
FIG. 3 is an angled view of the shoulder sling as worn by the patient at 40 degrees of flexion at the right glenohumeral joint

With reference to FIG. 1, shoulder sling device 100 is shown as worn by a user in accordance with the present invention. Device 100 consists of shoulder sling portion 200 from which emerges a plurality of straps, namely strap 1, strap 2 and strap 3. Referring to FIGS. 1-3, strap 1 is shown to emerge from the most superior portion of shoulder sling portion 200, extend across the patient's dorsum, return anteriorly by crossing the patient over the left trapezius muscle, pass through length adjusting mechanism 1A and loop into in attachment element 1B to return into the length adjusting mechanism. Attachment element 1B will be inserted into attachment retaining element 1C located on the anterior area of the device 100. The length of strap 1 may be adjusted via length adjusting mechanism 1A by pulling on strap 1. Similarly, strap 2 begins from a more posteriolateral location on the device, crosses the patients back, emerges anterior after crossing the patient's left axillary region to pass through length adjusting mechanism 2A, loop into attaching element 2B and return to the length adjusting mechanism. Attaching element 2B will be inserted into attachment retaining element 2C located on the anteriomedial of the shoulder sling portion 200. The length of strap 2 may be adjusted via length adjusting mechanism 2A by pulling on strap 2.

Referring to FIGS. 1-5, Strap 3 emerges from the lateral surface of the sling 200 and descends to length adjusting mechanism 3A, after which it descends to the lateral surface of elbow elevating support 300 where it passes through elbow strap guiding element 3B. Elbow strap guiding element 3B may run through the partial or entire length of the elbow elevating support 300. Strap 3 then emerges medially, ascends towards the medial surface of sling 200 and loops through strap looping element 3C (shown in FIGS. 3,5) on the shoulder sling portion 200, after which it descends to reenter elbow strap guiding element 3B. From here it emerges laterally and enters length adjusting 3A once again. This orientation allows for length adjustment of strap 3 which will symmetrically raise elbow elevating support 300.

Straps 1,2,3 may be constructed from a variety of different materials, including but not limited to leather, cotton, nylon, elastic/non-elastic cord, shock cord, web, woven elastic, elastic lace, polyester, polymers, denim, braid, and/or combinations and/or mixes of these materials, or any other material obvious to one in the art. Similarly, elbow strap guiding element may be constructed and/or coated with similar materials that allow for reduced friction against strap 3. Attachment elements 1B, 2B, 3B, attachment retaining elements 1C, 2C, 3C, and length adjusting mechanisms 1A, 2A, 3A may be assembled from a variety of devices for attachment. This includes, but is not limited to a conventional prong belt buckle, web strap buckle, snap hooks, cam buckles, hook clips, adjusters, web strap slides, carabiners, luggage clips, hook and loops mechanisms (Trademark Velcro) or any other material obvious to one in the art.

The straps, attachment and length adjustment mechanisms serve merely to initially mount the device 100 on the patient. An initial gross adjustment of the strap length will adjust the device to the patients overall size but will not provide any fine adjustment specific to an individual's body contours. Such fine adjustment will be discussed later.

Figure 5:
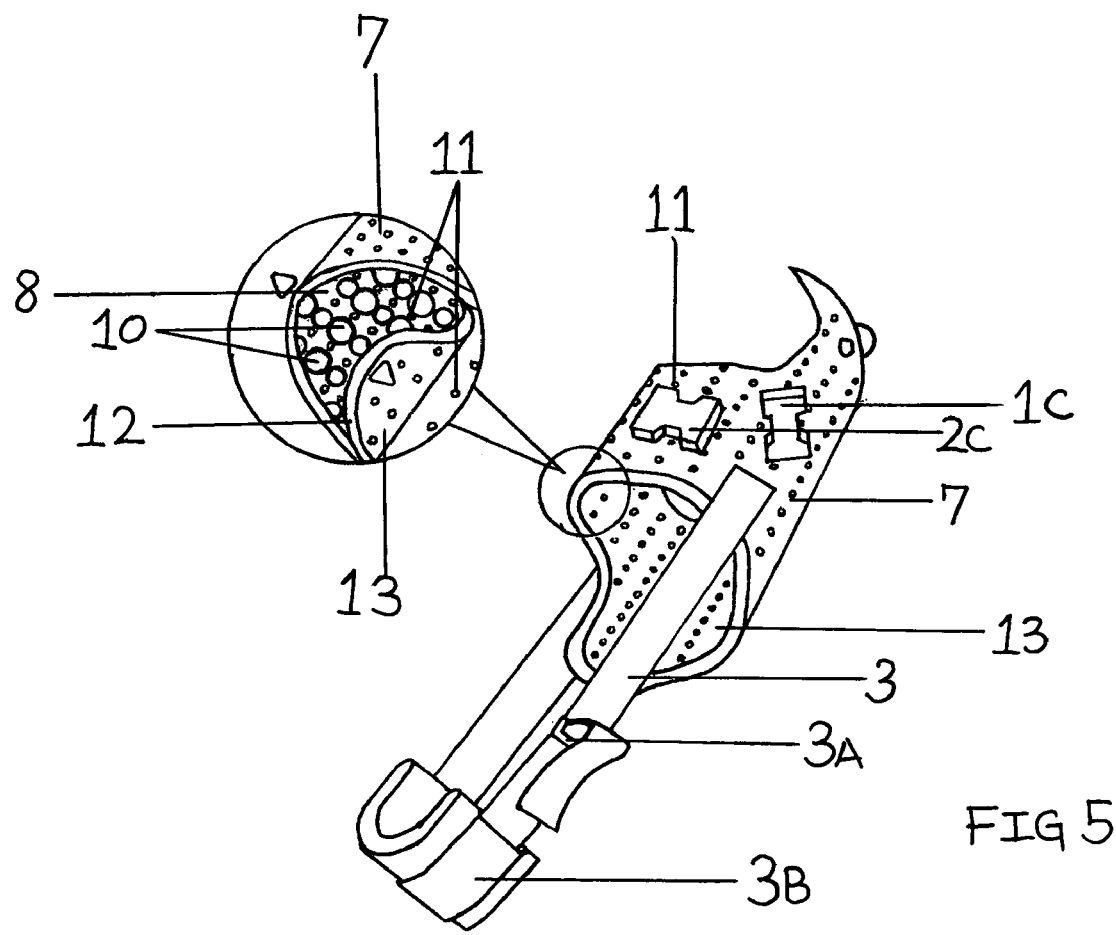
FIG. 5 is perspective view of the anteriolateral view of the shoulder sling with layers exposed

With regard to the initial mounting of the device on the patient, refer to FIG. 5. Shoulder sling portion 200 is shown to be continuous through its circumference. The figure depicts a region that is drawn transparent to allow the viewing of open region 400. In this orientation, the shoulder sling portion will be initially mounted on a user by inserting the user's arm into the open region and sliding the device up the desired arm. Subsequent securing of the device will be achieved via the attachment of straps 1, 2, and 3 into their respective attachment retaining elements.

Figure 4:
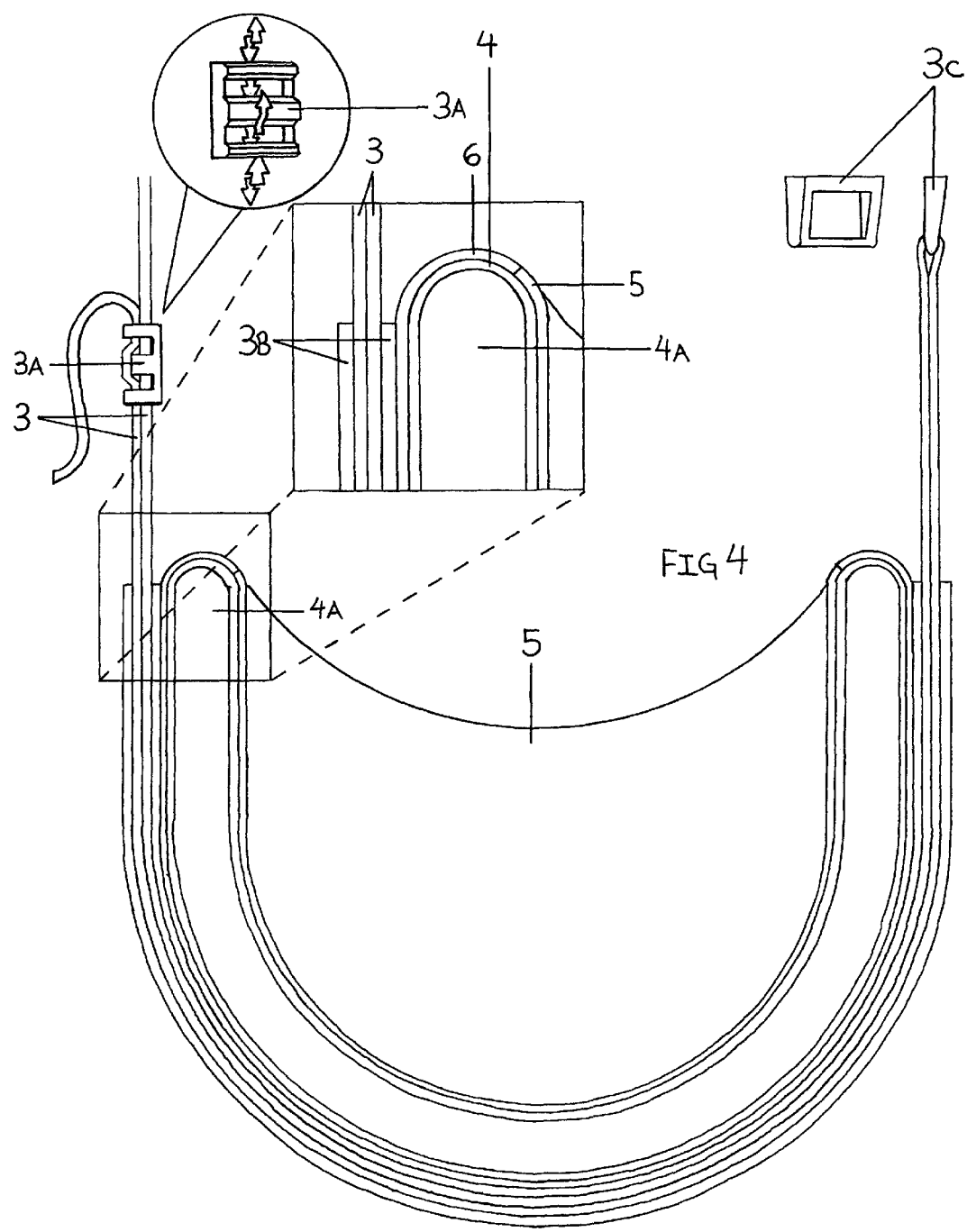
FIG. 4 is an anterior view of the elbow elevating support in accordance with the present invention.

Referring now to FIG. 4, elbow elevating support 300 is depicted in an anterior view, as well as in coronal section to illustrate its various components. Beginning from its exterior, elbow strap retaining mechanism 3B is shown to allow passage of strap 3 throughout its entire length. Interior to the elbow strap retaining mechanism 3B is the cushioning element housing wall 4 which retains cushioning element 4A. Cushioning element 4A may be constructed of a variety of different malleable materials, including but not limited to different varieties of foam such as flexible soft polyurethane foam, as well as highly viscoelastic pliable polymer gel materials as found in gel seats and/or mouse pads. Cushioning element 4A will provide a comfortable cushion to the user's elbow. Exterior to the more interior cushioning element housing wall is an interior textile layer 5, which will contact the skin of the user's elbow region. This interior textile layer 5 can be constructed from a variety of different materials, including but not limited to cotton, polyester blends, neoprene, fleece, satin, suede, any other fabric or cloth, blends thereof as well as any other material obvious to one in the art. The equivalent of the interior textile layer 5 of the exterior surface of the elbow elevating support 300 is the exterior textile layer 6, which will be constructed of a less pliable material including but not limited to leather, cotton, nylon, wool, denim, polyester, polymers, blends and/or combinations thereof, as well as any other material obvious to one in the art.

Figure 6:
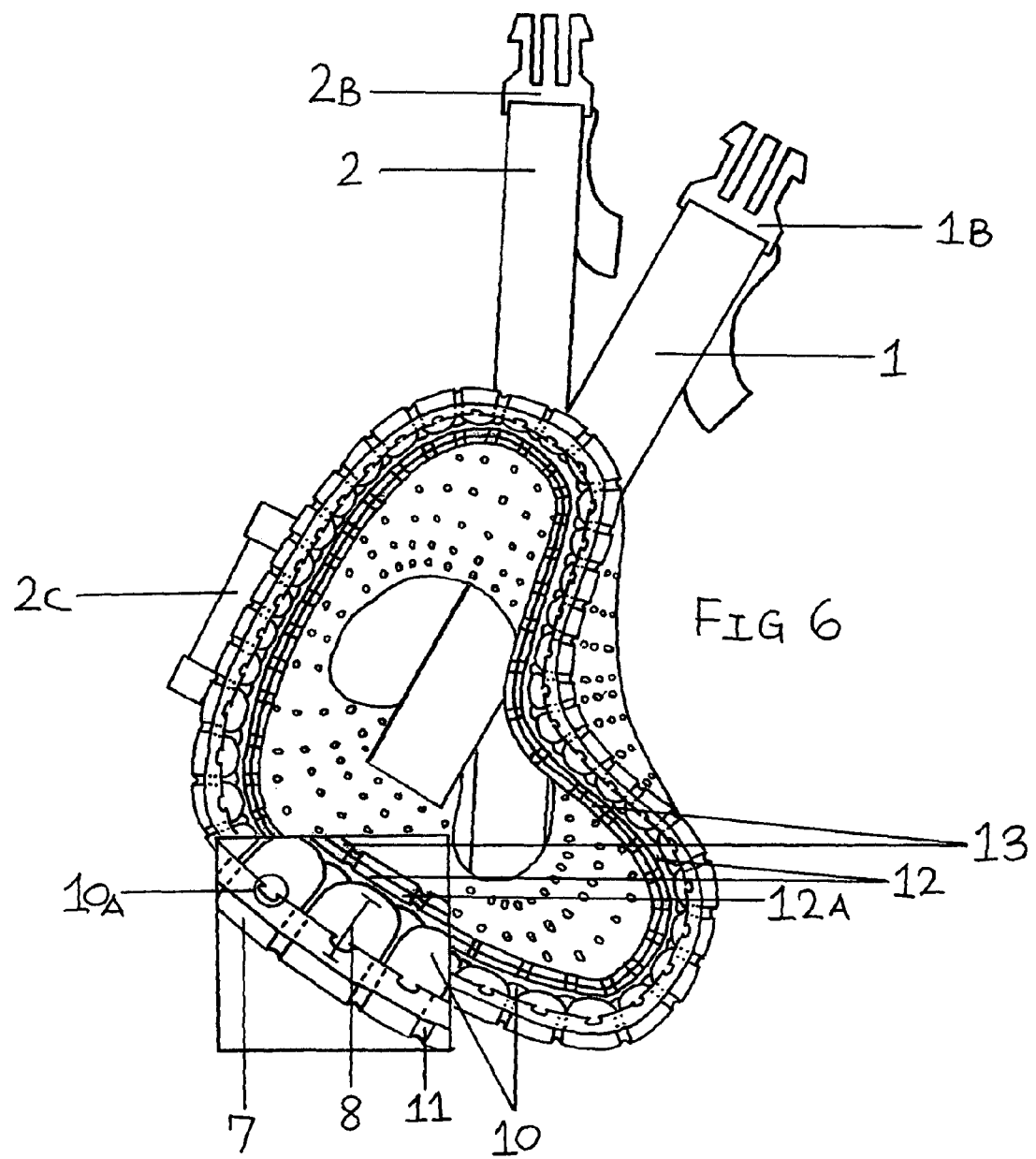
FIG. 6 is a cross sectional view of the shoulder sling
Figure 7:
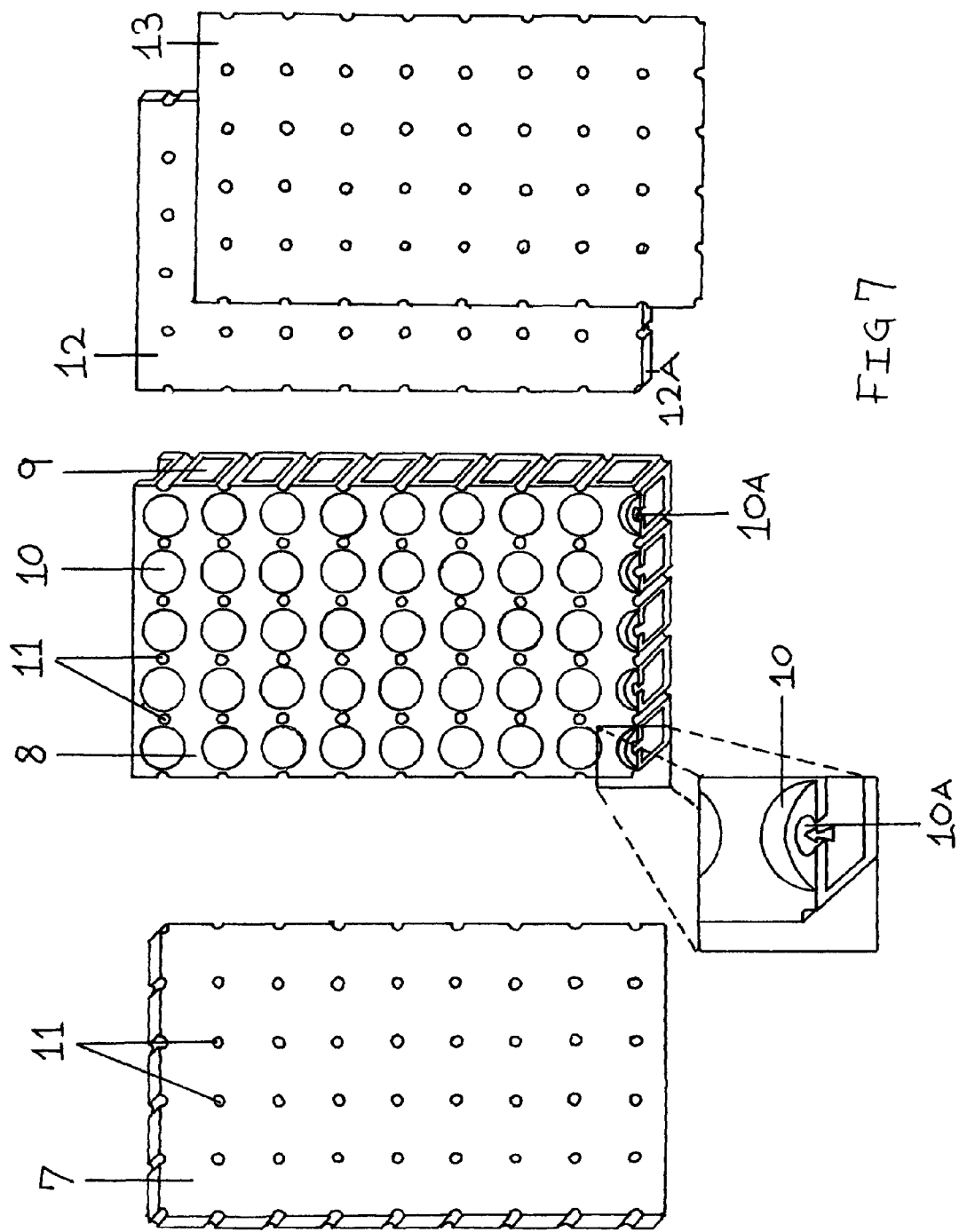
FIG. 7 is an exploded view of the shoulder sling

Referring now to FIG. 5, an anteriolateral perspective view of the shoulder sling as worn of the left arm is shown with component layers exposed in a zoomed in section. These layers can be better visualized in FIGS. 6 and 7. FIG. 6 depicts a cross sectional view of the shoulder sling portion 200 depicting its internal structures, which can be seen better in the zoomed in portion of the figure. The exterior surface of the sling is lined by an exterior textile layer 7 that is similar in construction to exterior textile layer 6 of the elbow elevating support 300. The interior surface of the sling is lined by an interior textile layer 13 that is similar in construction to interior textile layer 5 of the elbow elevating support 300. External to the internal textile layer is a cushioning element housing wall 12 which contains cushioning element 12A. The cushioning element 12A is similar to the cushioning element 4A of the elbow elevating support 300. In a preferred embodiment, the cushioning element 12A consists of a highly viscoelastic pliable polymer gel material. This gel material is preferentially elastomeric with the consistency of fatty tissue, such as T-Gel, a trademark of AliMed. External to the cushioning element housing wall is a unique air bladder 8. Air bladder 8 is shown to comprise a continuous air chamber space 9 and air bubbles 10. These elements are better shown in an exploded view as depicted in FIG. 7. The air bladder is depicted in zoomed section which allows a better visualization of air bubble inlet 10A.

Referring to FIGS. 5-7, note that ventilation holes 11 extend from the interior aspect of the device to its exterior. These ventilation holes are not continuous with the air bladder 8. They pass through the air bladder between the aforementioned air bubbles. These ventilation holes prevent the buildup of heat and sweat on the user's skin by allowing the escape of warm air and the subsequent physiological cooling. This aspect of the invention allows for greater comfort of use which will translate into greater compliance.

Figure 8:
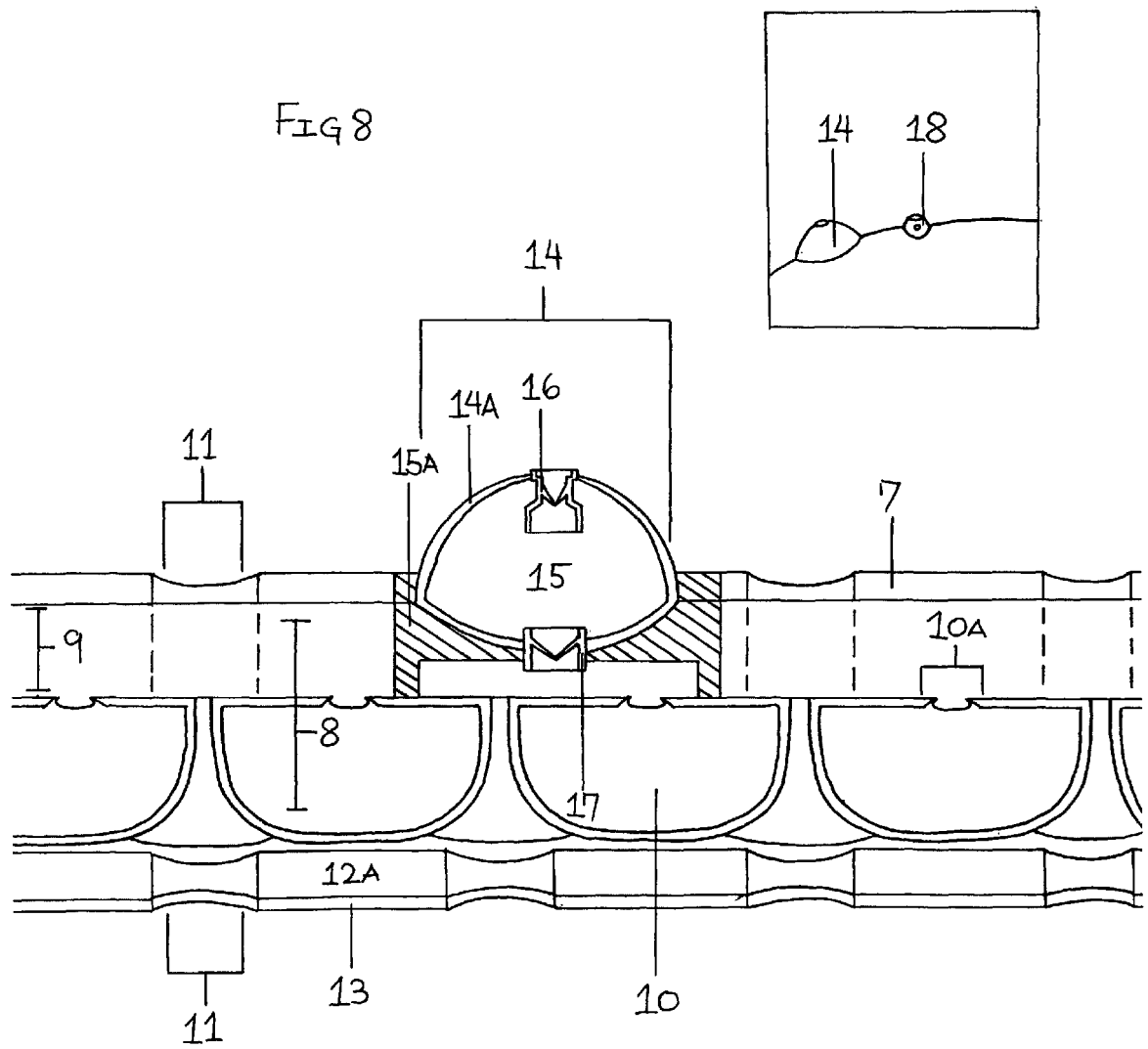
FIG. 8 is a view of the pump in accordance with the present invention

Referring back to FIGS. 1-3, an inflation mechanism 14 is depicted on the anterior surface of the shoulder sling portion. Details of the inflation mechanism are depicted in FIG. 8. Inflation mechanism 14 is shown to comprise collapsible inflation mechanism housing 14A, as well as one way valves 16 and 17, and is continuous with air chamber 8. The inflation mechanism is depressed with a user's finger, a process which will cover one way valve 15 to prevent air in inflation mechanism chamber area 15 from escaping into the atmosphere. The depression of the inflation mechanism 14 will force the opening of one way valve 17 and allow entry of air into the continuous air bladder space 9 of air bladder 8. The inflation mechanism 14 is held in place via inflation mechanism retaining element 15A. This component passes through all layers exterior to the air bladder 8 and terminates at the air bladder. It will not only maintain the integrity of the inflation mechanism 14, but will allow the passage of air into the air bladder without fail. Once the air enters the air bladder, it will travel to areas with a negative pressure gradient, with greater distribution to areas with a larger pressure gradient. During inflation, the air will enter air bubbles 10 via air bubble inlet 10A as shown in FIG. 7. These bubbles will inflate until a point where they provide adequate and comfortable support to the patient's shoulder. In a preferred embodiment, the inflation of the bubbles will distribute and deform the cushioning element 12A and allow for a snug, comfortable fit. When the air bubbles are optimally inflated to adjust to an individual body contour, the pressure gradient will dissipate in this area and the inflated air will preferentially distribute to more distal air bubbles in need of inflation. Note that the dashed lines of FIG. 8 represent the ventilation hole 11 that passes through the air chamber 8 and is not continuous with air chamber 8.

Figure 9:
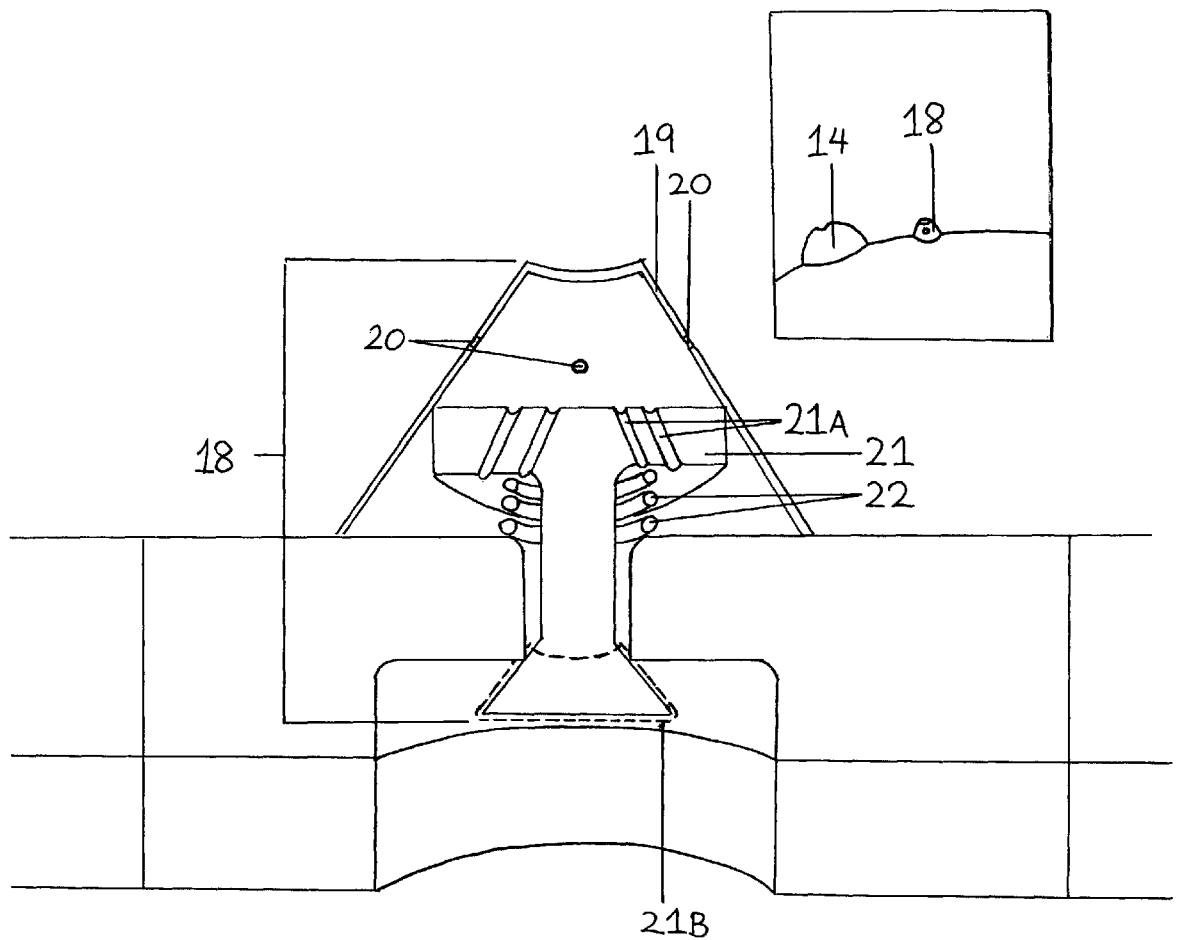
FIG. 9 is a view of the release valve in accordance with the present invention

Referring back to FIGS. 1-3, a pressure releasing mechanism 18 is shown on the anterior surface of the shoulder sling portion. Details of the pressure releasing mechanism are depicted in FIG. 9, which depicts it in coronal section. Pressure releasing mechanism 18 comprises a semi-rigid collapsible pressure releasing mechanism housing 19 which is penetrated with a plurality of symmetric spaced pressure releasing air outlets 20. The pressure releasing mechanism housing 19 contains a pressure releasing valve 21 which penetrates air chamber 8. The pressure releasing valve 21 is maintained in an upright position via resilient buoyant pressure retaining mechanism 22, which prevents air from escaping from the air chamber 8. Similar to the inflation mechanism retaining element 15A, the integrity of the pressure releasing mechanism is maintained by pressure releasing mechanism retaining element 19A, which also passes through all layers exterior to the air bladder 8 and terminates at the air bladder. When a user depresses the pressure releasing mechanism 18 with his/her finger, the pressure releasing mechanism housing 19 will collapse and allow the depression of pressure releasing valve 21. The depression of the pressure releasing valve will compress the buoyant pressure retaining mechanism 22 which will depress the tail of the pressure releasing valve and allow the escape of air up, through a plurality of air passage mechanism 21A in the head of the pressure releasing valve 21 and out through the pressure releasing air outlets 20. When depression of the pressure releasing mechanism is released, the buoyant pressure retaining mechanism 22 will cause the aforementioned pressure releasing valve to rise again. In this orientation, further escape of air from the air bladder 8 into the atmosphere is prevented, for the contact interface between the pressure releasing valve 21 and pressure releasing mechanism retaining element 19A is inherently airtight.

The collapsible inflation mechanism housing 14A, collapsible pressure releasing mechanism housing 19, as well as buoyant pressure retaining mechanism 22 may be constructed from any resilient, buoyant material such as rubber, polymers, and/or any other material obvious to one in the art. One way valves and pressure releasing valve 21 may be constructed of a metal, rubber, polymer or any other material obvious to one in the art. Moreover, pressure releasing valve 21 may further comprise airtight lining element 21B, which may be constructed of similar materials to perform the desired function. The air chamber and air bubbles may be made of an airtight polymer, rubber, and/or any other material obvious to one in the art. Inflation mechanism retaining element 15A, and pressure releasing mechanism retaining element 19A may be constructed of rubber or any other material capable of performing the stated function that is apparent to one in the art, such that the inflation mechanism and pressure releasing mechanism, respectively, are maintained in position, and that interface between the pressure releasing valve 21 is airtight.

In summary, referring to FIG. 1,3, or 5, upon donning the device 100 via straps 1 and 2, the user will insert his/her elbow into the elbow elevating support 300 and adjust its height via tugging on strap 3. After this gross adjustment of the shoulder sling device 100 is completed, the user will inflate the air bladder 8 within the shoulder sling portion 200 via multiple depressions of inflation mechanism 14 which will preferentially distribute air to desired air bubble 10 areas due to a differential negative pressure gradient. When the desired snug fit is achieved, the user will cease to depress the inflation mechanism 14 and pressure will be retained via one way valve 18, and a small amount of air will be retained in the inflation mechanism chamber. The fit will thus remain snug throughout the use of the apparatus. Comfort of use is granted via a comfortable inner textile layer at both the elbow elevating support 300 and shoulder sling 200, as well as ventilation holes 11 at the shoulder sling 200 that will allow the escape of warm air, prevent sweat buildup, and allow physiologic cooling. If the inflated pressure if too high, or if the user desires to remove the device, he/she will depress the pressure releasing mechanism 18 which will allow the escape of air from the air bladder and decrease the pressure.

Having thus described details of preferred embodiments in accordance with the scope of the present invention it is apparent that it provides numerous benefits over, and addresses inadequacies of the prior art. It should be apparent to one skilled in the art that various adaptations of modifications of the present invention can be made and will still fall within its scope, which is limited only by the appended claims:

The invention claimed is:

1. An inflatable device adapted to prevent joint subluxation, the device is adapted to encompass and contour one or more body surfaces on each side of a desired jointed that is being treated and span more than one joint, the device comprises a plurality of straps adapted to envelop both anterior and posterior surfaces of the user's body, a joint subluxation portion that is adapted to prevent joint subluxation of at least one joint, an elevating support portion adapted to provide lift across a body joint, said subluxation portion and said elevating support portion comprise non-continuous layers, each layer being made of different materials, the exterior of said plurality of non-continuous layers comprise a material that is less pliable than the interior most layers of said non-continuous layers.

2. The inflatable device of claim 1 wherein said plurality of straps are further comprised of a length adjusting means that allows the shortening and lengthening of said plurality of straps.

3. The inflatable device of claim 2 wherein said plurality of straps further comprise an attachment means which insert into an attachment means retaining element located on said joint subluxation prevention portion of said device after enveloping said user's body, after which said device will remain secured to said user's body and function to maintain the integrity of the joint.

4. The inflatable device of claim 3 wherein said plurality of straps extend across a patient's dorsum and emerge anteriorly.

5. The inflatable device of claim 4 wherein the exterior most of said plurality of non-continuous layers comprises a material that is less pliable than that of said interior most layer and serves to provide some rigidity and maintain the form of the said device.

6. The inflatable device of claim 1 further comprising a layer comprising a cushioning means.

7. The inflatable device of claim 6 where said cushioning means comprises a cushioning means housing that contains malleable material.

8. The inflatable device of claim 6 where said malleable material comprises a highly viscoelastic pliable polymer gel.

9. The inflatable device of claim 6 where said malleable material comprises flexible soft foam.

10. The inflatable device of claim 1 further comprising an air bladder that is continuous throughout its construction, forming a continuous air bladder space and formed of an airtight polymer material.

11. The inflatable device of claim 10 wherein said air bladder is comprised of equidistantly arranged air bubbles that comprises an air bubble inlet that is continuous with said continuous air bladder.

12. The inflatable device of claim 1 further comprising a manual inflation means located on said joint subluxation prevention portion continuous with said continuous air bladder space that is operated by a user utilizing one or more fingers.

13. The inflatable device of claim 12 wherein said manual inflation means is comprised of a semi-rigid collapsible inflation means housing that is depressed and elevated by said user operation and encloses a inflation means chamber that comprises atmospheric air.

14. The inflatable device of claim 12 wherein the said manual inflation means is maintained in position by an inflation means retaining element.

15. The inflatable device of claim 13 wherein said manual inflation means comprises a plurality of one way valves, whereby the depression of said manual inflation means will force captured said air in said inflation means chamber through said valves into said continuous air space and prevent its escape to the external environment, wherein said air will inflate said air bladder and said air bubbles pushing and deforming said malleable material against the user's body part, whereby said air bubbles will inflate according to individual pressure requirements against said user's body and provide a fit that is customized to an individual's body contours and asymmetries to provide uniform support of the joint and reduce the chance of development of pressure ulcers and joint subluxation.

16. The inflatable device of claim 15 further comprising a pressure releasing means located on said joint subluxation prevention portion continuous with said continuous air bladder space that is operated by a user utilizing one or more fingers.

17. The inflatable device of claim 15 wherein said pressure releasing means is located adjacent to said manual inflation means.

18. The inflatable device of claim 16 wherein said pressure releasing means is comprised of a semi-rigid pressure releasing means housing that is depressed and elevated by said user operation.

19. The inflatable device of claim 16 wherein said pressure releasing means housing further comprises of a plurality of pressure releasing air outlets.

20. The inflatable device of claim 16 wherein said pressure releasing means is comprised of a pressure releasing valve that will allow the escape of captured air in said air bladder when operated by user.

21. The inflatable device of claim 19 wherein said pressure releasing means further comprises a buoyant pressure retaining means which retains said pressure releasing valve in an orientation that prevents the escape of said captured air when said pressure releasing means is not operated by the user.

22. The inflatable device of claim 1 further comprising a pressure releasing means retaining element that maintains the pressure releasing means in place and furthermore contacts said pressure releasing valve when said pressure releasing means is not operated by the user such that the escape of said captured air is prevented.

23. The inflatable device of claim 21 wherein said pressure releasing valve comprises an air passage means through which said captured air will escape.

24. The inflatable device of claim 1 wherein said joint subluxation prevention portion and said elevating support portion are comprised of ventilation holes that passes through all said layers, allowing for the cooling of said user's skin.

25. The inflatable device of claim 1 wherein said elevating support portion comprises a strap retaining means that allows the passage of one of said plurality of straps throughout its entire length.

* * * * *